(12) United States Patent
Shimada et al.

(10) Patent No.: US 8,313,448 B2
(45) Date of Patent: Nov. 20, 2012

(54) WALKING ASSISTANCE DEVICE

(75) Inventors: Kei Shimada, Wako (JP); Ken Yasuhara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 702 days.

(21) Appl. No.: 12/536,525

(22) Filed: Aug. 6, 2009

(65) Prior Publication Data

US 2010/0036302 A1 Feb. 11, 2010

(30) Foreign Application Priority Data

Aug. 7, 2008 (JP) ................. 2008-203803

(51) Int. Cl.
*A61H 1/00* (2006.01)
*A61F 5/00* (2006.01)
*A61B 5/117* (2006.01)

(52) U.S. Cl. ............... 601/5; 602/23; 600/595

(58) Field of Classification Search .......... 601/5, 33–35, 601/23; 482/51, 66; 623/27, 34, 53; 602/23, 602/16, 19, 5; 600/595, 331, 901
See application file for complete search history.

(56) References Cited

U.S. PATENT DOCUMENTS

| 7,537,573 B2 * | 5/2009 | Horst | 601/5 |
| 2009/0199883 A1 * | 8/2009 | Hiki | 135/65 |

FOREIGN PATENT DOCUMENTS

| JP | 6-189995 A | 7/1994 |
| JP | 11-253475 A | 9/1999 |
| JP | 2006-75226 | 3/2006 |
| JP | 2006-334200 A | 12/2006 |
| JP | 2007029113 A | 2/2007 |
| JP | 3955304 B2 | 8/2007 |
| WO | WO 2009082249 A2 * | 7/2009 |

OTHER PUBLICATIONS

JP Office Action dated May 29, 2012, corresponding to JP Application No. 2008-203803.

* cited by examiner

*Primary Examiner* — Loan Thanh
*Assistant Examiner* — Tarla Patel
(74) *Attorney, Agent, or Firm* — Squire Sanders (US) LLP

(57) ABSTRACT

The present invention provides a walking assistance device comprising a pelvis support member (10) adapted to be worn on a hip of a wearer; a thigh support member (20) adapted to be worn on a thigh of the wearer; a leg support member (40) adapted to be worn on a leg of the wearer; a knee joint hinge (60) disposed at a position corresponding to a side part of a knee of the wearer and connecting the leg support member (40) to the thigh support member (20) in a manner that enables back-and forth rotation of the leg support member (40) with respect to the thigh support member (20); and a power generator assembly (100) mounted to the pelvis support member (10) at a position corresponding to a side part of a hip joint of the wearer; wherein the power generator assembly (100) comprises a hip joint power generator (110) and a knee joint power generator (120) each having an output member (116, 126, respectively), with the output member (116) of the hip joint power generator (110) being connected to the thigh support member (20) in a power-transmittable manner and the output member (126) of the knee joint power generator (120) being connected to the leg support member (40) via a power transmitting mechanism (90) which transmits power generated by the knee joint power generator (120) to the leg support member (40).

11 Claims, 6 Drawing Sheets

Fig.5
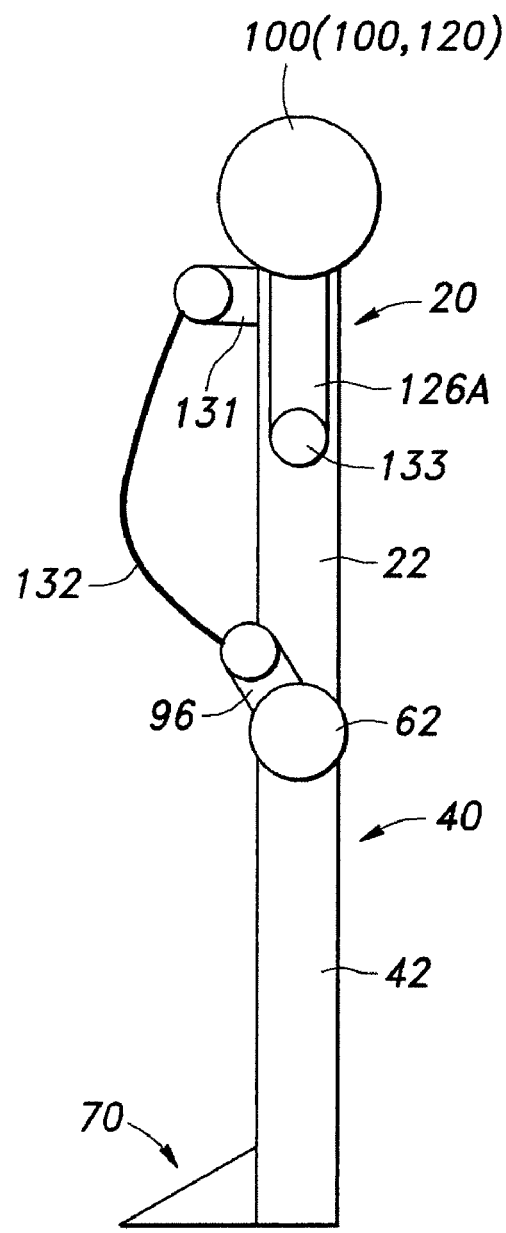
(a)
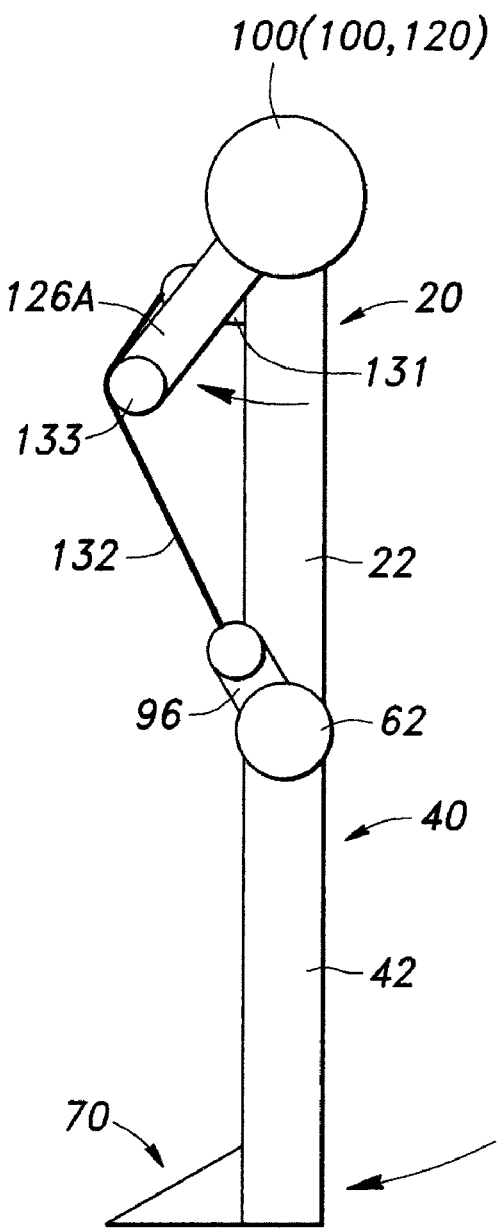
(b)

(a)   (b)

WALKING ASSISTANCE DEVICE

TECHNICAL FIELD

The present invention relates to a walking assistance device, especially to a walking assistance device for assisting a person with impaired motor function of lower limbs in walking.

BACKGROUND OF THE INVENTION

There is known a walking assistance device for assisting a person with impaired motor function of the lower limbs, caused by lesion or advanced age, in walking, comprising a pelvis support member adapted to be worn on a pelvis of a wearer, a thigh support member adapted to be worn on a thigh of the wearer, a leg support member adapted to be worn around a leg of the wearer, a knee joint hinge disposed at a position corresponding to a side part of a knee of the wearer and connecting the leg support member to the thigh support member in a manner that enables back-and-forth rotation of the leg support member with respect to the thigh support member, a hip joint electric motor disposed at a position corresponding to a side part of a hip joint of the wearer for providing the thigh support member with an assisting force to assist the movement of the thigh, and a knee joint electric motor mounted to the knee joint hinge for providing the leg support member with an assisting force to assist the movement of the leg (see, for example, Japanese patent laid open publication No. 2006-75226).

The above-mentioned walking assistance device has 4 electric motors, each two of which are placed on either side of the device, and thus is capable of assisting the movement of the thighs using the output of the hip joint electric motors and the movement of the legs using the output of the knee joint electric motors.

In the above-mentioned walking assistance device, as the knee joint electric motor is disposed on the knee joint, the hip joint electric motor rotates the thigh support member along with the knee joint electric motor, and thus the load on the hip joint electric motor increases, thereby increasing its power consumption. In addition, if the electric motor, which is a heavy load, is disposed on the knee joint whose movement range is broad, the inertia mass of the knee of the wearer increases, thereby hampering the natural walking sense and disrupting the walking pace of the wearer.

BRIEF SUMMARY OF THE INVENTION

In view of such problems of the prior art, a primary object of the present invention is to reduce the load on the hip joint electric motor and to prevent the natural walking sense from being hampered, thereby achieving appropriate walking assistance while reducing the discomfort that the wearer may feel.

The walking assistance device of the present invention comprises a pelvis support member adapted to be worn on a hip of a wearer, a thigh support member adapted to be worn on a thigh of the wearer, a leg support member adapted to be worn on a leg of the wearer, a knee joint hinge disposed at a position corresponding to a side part of a knee of the wearer and connecting the leg support member to the thigh support member in a manner that enables back-and-forth rotation of the leg support member with respect to the thigh support member, a power generator assembly mounted to the pelvis support member at a position corresponding to a side part of a hip joint of the wearer, wherein the power generator assembly comprises a hip joint power generator and a knee joint power generator each having an output member with the output member of the hip joint power generator being connected to the thigh support member in a power-transmittable manner and the output member of the knee joint power generator being connected to the leg support member via a power transmitting mechanism which transmits power generated by the knee joint power generator to the leg support member.

According to the walking assistance device of the present invention, as the knee joint electric motor is disposed at a position corresponding to a side part of the hip joint of the wearer along with the hip joint electric motor instead of a position corresponding to the knee joint, the load on the hip joint electric motor becomes less as compared to when the knee joint electric motor is disposed on the knee. In addition, the increase in the inertia mass of the knee joint which would be caused if the knee joint electric motor were disposed on the knee joint can be avoided, thereby preventing the walking sense of the wearer from being hampered by such increase in the knee joint inertia mass. This achieves appropriate walking assistance while reducing the discomfort that the wearer may feel. Furthermore, the walking assistance device can be configured such that the inertia mass of the device decreases in the direction from the thigh support member to the leg support member, thereby enabling walking assistance without hampering the natural walking sense.

Moreover, since the knee joint power generator is disposed near body trunk at a side part of the hip joint, where the amount of the displacement with respect to the body trunk is significantly small during walking, the load caused by the inertia moment of the knee joint can be prevented from being increased by the displacement of the knee joint power generator.

In the walking assistance device of the present invention, preferably, the power generator assembly comprises a fixed case member mounted on the pelvis support member, the hip joint power generator and the knee joint power generator each comprise an electric motor having a stator member and a rotor member connected to the corresponding output member, the stator member of the hip joint power generator being fixedly attached to the fixed case member, and the stator member of the knee joint power generator being fixedly attached to the output member of the hip joint power generator and connected to the rotor member of the hip joint power generator.

According to the walking assistance device of the present invention, as the knee joint power generator is connected to the rotor member of the hip joint power generator, when the hip joint rotates according to the rotation of the hip joint power generator, it displaces the knee joint, and the knee joint power generator rotates according to the displacement of the knee joint, and thus the rotation of the knee joint power generator necessary for appropriate rotation of the knee joint is easily determined based on the current position of the knee joint, which has been changed by the rotation of the hip joint.

The walking assistance device of the present invention preferably further comprises a first stopper mechanism for determining a maximum rotation angle range of the rotor member of the hip joint power generator with respect to the fixed case member and a second stopper mechanism for determining a maximum rotation angle range of the rotor member of the knee joint power generator with respect to the rotor member of the hip joint power generator. In addition, the walking assistance device of the present invention further comprises a third stopper mechanism for determining a maximum rotation angle range of the rotor member of the knee joint power generator with respect to the fixed case member.

According to the walking assistance device of the present invention, the first stopper mechanism and the second stopper mechanism achieve the motion of the hip joint and the knee joint in natural normal walking, respectively, thereby ensuring appropriate walking assistance without hampering the natural walking sense.

In the walking assistance device of the present invention, preferably, the power generator assembly is supported at the pelvis support member via a hinge in a manner that enables it to rotate with respect to the pelvis support member in a lateral direction of the wearer. Furthermore, the knee joint hinge has a hinge element enabling the knee joint hinge to rotate in a lateral direction of the wearer.

According to the walking assistance device of the present invention, as the power generator assembly is supported at the pelvis support member in a manner that enables it to rotate with respect to the pelvis support member in a lateral direction of the wearer, it does not hamper the wearer from spreading his/her legs laterally. In addition, since the knee joint hinge can rotate in a lateral direction of the wearer as well, it does not hamper the wearer from spreading his/her legs either.

In the walking assistance device of the present invention, preferably, the thigh support member comprises a frontal thigh pad for abutting the frontal part of the thigh of the wearer and a dorsal thigh pad for abutting the dorsal part of the thigh of the wearer.

According to the walking assistance device of the present invention, as the frontal thigh pad and the dorsal thigh pad abut the frontal and dorsal part of the thigh respectively, the walking assistance force can be surely provided to the thigh.

In the walking assistance device of the present invention, preferably, the leg support member comprises a frontal leg pad for abutting the frontal part of the leg of the wearer near the knee and a dorsal leg pad, positioned at a lower height compared to the frontal pad, for abutting the dorsal part of the leg of the wearer of the wearer near a malleolus.

According to the walking assistance device of the present invention, as the frontal leg pad and the dorsal leg pad abut the leg at different heights, the torque necessary for the appropriate motion of the leg around the knee joint in walking can be effectively provided to the leg while minimizing the discomfort that the wearer may feel.

The walking assistance device of the present invention preferably further comprises a foot support member for supporting a foot of the wearer and a foot joint hinge disposed at a position corresponding to a side part of a foot joint of the wearer and connecting the foot support member to the leg support member in a manner that enables back-and forth rotation of the foot support member with respect to the leg support member.

According to the walking assistance device of the present invention, the foot lack motion freedom other than plantar flexion and dorsal flexion, therefore even if the wearer is almost incapable of moving and controlling his/her legs, the foot can be prevented from being moved in an uncontrolled manner with inversion and eversion, and thus the foot can be restrained in order to maintain its motion stability.

The walking assistance device of the present invention preferably comprises a sole supporting portion for supporting a sole of the wearer and receiving the floor reaction force.

According to the walking assistance device of the present invention, as the sole supporting portion receives floor reaction force, the wearer receives less floor reaction force, and thus the load on the feet of the wearer can be reduced significantly.

The power transmitting mechanism of the present invention preferably has a four-bar linkage structure.

The power transmitting mechanism of the present invention preferably comprises a flexible wire connecting the thigh support member to the knee joint hinge, and a tension providing member for selectively providing tension to the flexible wire using the power generated by the knee joint power generator.

According to the walking device of the present invention, as the knee joint power generator is disposed at a position corresponding to a side part of the hip joint of the wearer along with the hip joint power generator instead of a position corresponding to the knee joint, the load on the hip joint electric motor becomes less as compared to when the knee joint electric motor is disposed on the knee. In addition, the increase in the inertia mass of the knee joint which would be caused if the knee joint power generator were disposed on the knee joint can be avoided, thereby preventing the walking sense of the wearer from being hampered by such increase in the knee joint inertia mass. This achieves appropriate walking assistance while reducing the discomfort that the wearer may feel. Moreover, since the knee joint power generator is disposed near body trunk on a side part of the hip joint, where the amount of the displacement with respect to the body trunk is significantly small during walking, it will not be displaced significantly by walking, and thus the load caused by the inertia moment of the knee joint can be prevented from being increased by the displacement of the knee joint power generator.

BRIEF DESCRIPTION OF THE DRAWINGS

FIGS. 5(a) and (b) are schematic views showing another embodiment of the walking assistance device of the present invention in a standing position.

DETAILED DESCRIPTION OF THE PREFERRED EMBODIMENTS

An embodiment of the walking assistance device according to the present invention is described below in detail with reference to FIGS. 1-4.

Figure 1:
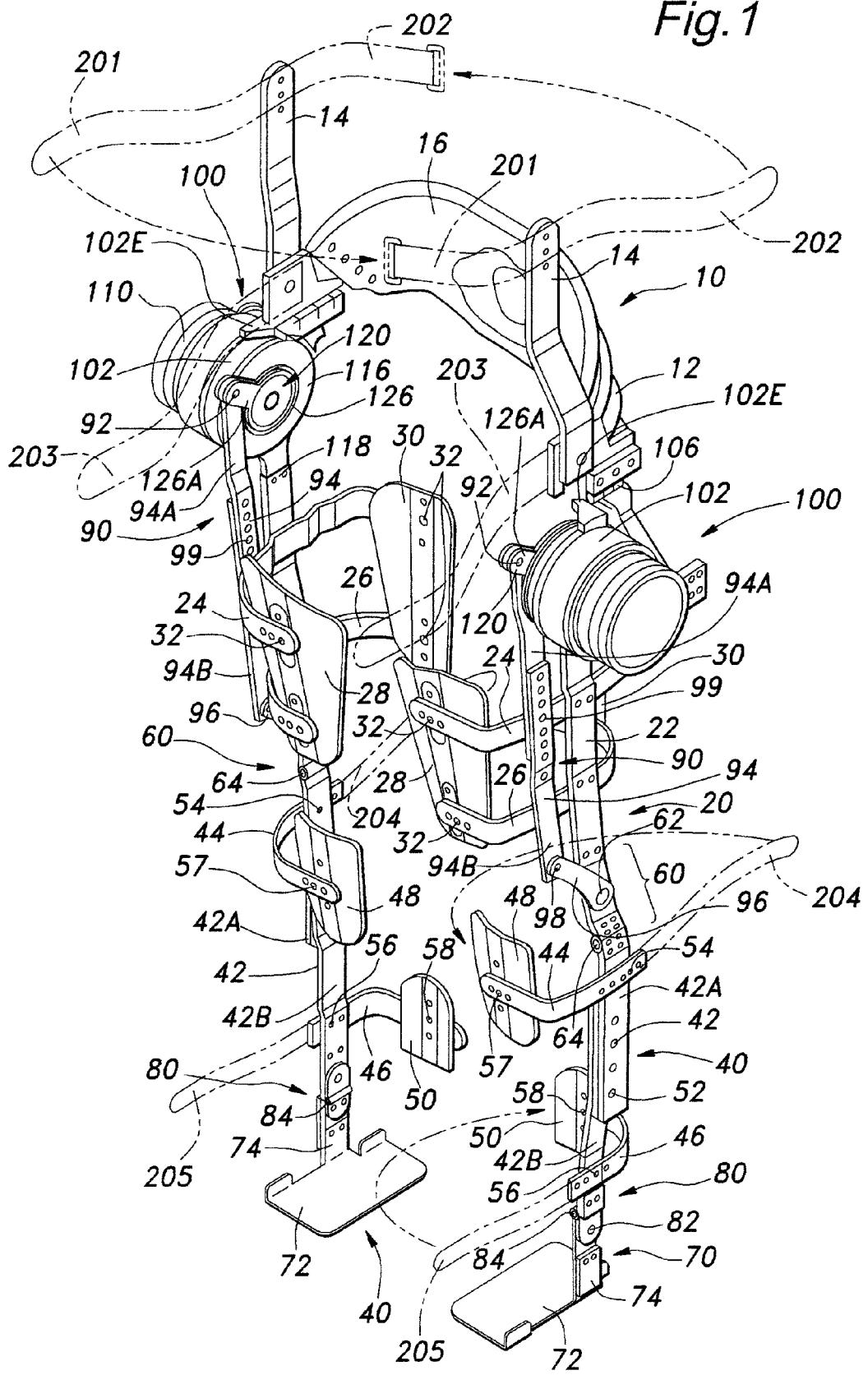
FIG. 1 is a perspective view showing an embodiment of the walking assistance device of the present invention.

As shown in FIG. 1, the walking assistance device of this embodiment mainly comprises a pelvis support member 10 adapted to be worn on the pelvis of the wearer, right and left thigh support members 20 adapted to be worn on the right and left thighs of the wearer, right and left leg support members 40 adapted to be worn on the right and left legs of the wearer, right and left knee joint hinges 60 disposed at positions corresponding to side parts of the right and left knee joints of the wearer and connecting the leg support members 40 to the thigh support members 20 in a manner that enables back-and forth rotation of the leg support members 40 with respect to the thigh support members 20, right and left foot support members 70 adapted to support the feet of the wearer, and right and left foot joint hinge 80 disposed at positions corresponding to side parts of the right and left foot joints of the wearer and connecting the foot support members 70 to the leg support members 40 in a manner that enables back-and-forth rotation of the foot support members 70 with respect to the leg support members 40.

The walking assistance device further comprises right and left power generator assemblies 100 mounted to the pelvis support member 10 at positions corresponding to side parts of the right and left hip joints of the wearer, and right and left power transmitting mechanisms 90.

The pelvis support member 10 comprises a metal pelvis frame 12 having the shape of letter-C as seen in plan view so as to engage the dorsal part of the pelvis, a pair of lateral support frames 14 each attached to either end of the frontal part of the pelvis frame 12, and a back pad 16 attached to the pelvis frame 12. The back pad 16 has a portion which abuts the sacral bone of the wearer when the device is worn. This portion contains a sponge and the like and thus is provided with elasticity. The lateral support frames 14 are provided with adjustable body trunk belts 201, 202 for securing the lateral support frames 14 to the body trunk. The pelvis frame 12 is provided with, at either end, an adjustable abdominal belt 203 so that the pelvis frame 12 fits the pelvis. The abdominal belt 203 may be adjusted by hook and loop fastener.

Each of the thigh support members 20 comprises a vertical bar 22, letter-C shaped springy pad support members 24 and 26 mounted, one above the other, to the vertical bar 22, a frontal thigh pad 28 attached to the frontal part of the pad support members 24 and 26 so as to abut the frontal part of the thigh of the wearer, and a dorsal thigh pad 30 attached to the dorsal part of the pad support members 24 and 26 so as to abut the dorsal part of the thigh of the wearer.

In detail, each of the pad support members 24 and 26 is fixed at its middle point to the internal surface of the vertical bar 22 in a horizontal posture, and thus extends forward and backward from the vertical bar 22. The frontal thigh pad 28 is fixed to the frontal part of the pad support members 24 and 26 such that it bridges the pad supports members 24 and 26. The dorsal thigh pad 30 is fixed to the dorsal part of the pad support members 24 and 26 such that it bridges the pad supports members 24 and 26. Thus the dorsal thigh pad 30 and the frontal thigh pad 28 are arranged at the same height in opposed positions.

Each of the frontal thigh pad 28 and the dorsal thigh pad 30 is secured by bolts at a middle point in the width direction to the pad support members 24 and 26 at an attaching portion 32. The attaching portion 32 includes a plurality of bolt holes so that the position of each pad can be adjusted both vertically and horizontally.

Therefore, the position of each of the frontal thigh pad 28 and the dorsal thigh pad 30 can be adjusted according to the body type and size of the wearer. The vertical bar 22 may consist of 2 components so as to be length-adjustable.

The frontal thigh pad 28 and dorsal thigh pad 30 may be made of metal or plastic and have elasticity to fit the thigh of the wearer.

Each of the leg support members 40 comprises a vertical bar 42, a letter-L shaped springy pad support member 44 attached to the upper end of the vertical bar 42 and extending forward therefrom, a letter-L shaped springy pad support member 46 attached to the lower end of the vertical bar 42 and extending backward therefrom, a frontal leg pad 48 attached to an end of the pad support member 44 so as to abut the frontal part of the leg of the wearer near the knee, a leg belt 204 attached to the pad support member 44 for fitting the frontal leg pad 48, a dorsal leg pad 50 attached to an end of the pad support member 46 so as to abut the dorsal part of the leg of the wearer near the malleolus, and a leg belt 205 attached to the pad support member 46 for fitting the dorsal leg pad 50. The dorsal leg pad 50 and the frontal leg pad 48 are arranged at different heights in opposed positions.

In detail, the vertical bar 42 consists of an upper member 42A and a lower member 42B which are secured to each other by bolts at an attaching portion 52. The attaching portion 52 includes a plurality of bolt holes so that the vertical bar 42 can be adjusted lengthwise. The pad support member 44 is secured by bolts to the upper member 42A at an attaching portion 54. The attaching portion 54 includes a plurality of bolt holes so that the position of the pad support member 44 can be adjusted horizontally. The pad support member 46 is secured by bolts to the lower member 42B at an attaching portion 56. The attaching portion 56 includes a plurality of bolt holes so that the position of the pad support member 56 can be adjusted horizontally.

The frontal leg pad 48 is secured to the frontal end of the pad support member 44 by bolts at an attaching portion 57. The attaching portion 57 includes a plurality of bolt holes such that the position of the frontal leg pad 48 can be adjusted vertically and horizontally. The dorsal leg pad 50 is secured to the back-end of the pad support member 46 by bolts at an attaching portion 58. The attaching portion 58 includes a plurality of bolt holes such that the position of the dorsal leg pad 50 can be adjusted vertically and horizontally.

Therefore, the positions of the frontal leg pad 48 and dorsal leg pad 50 can be adjusted according to the body type and size of the wearer. The leg belts 204 and 205 may be adjusted by hook and loop fastener.

The frontal thigh pad 28, the dorsal thigh pad 30, the frontal leg pad 48 and the dorsal leg pad 50 may each be made of metal plate or plastic and have elasticity to fit on the thigh and the leg of the wearer.

The knee joint hinge 60 is disposed at a position corresponding to a side part of the knee joint of the wearer, and connects the upper end of the vertical bar 42 of the leg support member 40 to the lower end of the vertical bar 22 of the thigh support member 20 via a shaft 62 in a manner that enables back-and-forth rotation of the vertical bar 42 with respect to the vertical bar 22. The knee joint hinge 60 has a hinge element 64 so that it can rotate in a lateral direction of the wearer around the hinge element 64 in addition to back-and-forth rotation.

The foot support member 70 comprises a sole supporting plate 72 which supports the sole of the wearer and receives floor reaction force, and a vertical bar 74 extending vertically upward from the sole supporting plate 72. The vertical bar 74 may be length-adjustable.

The foot joint hinge 80 is disposed at a position corresponding to a side part of the foot joint of the wearer and connects the upper end of the vertical bar 74 of the foot support member 70 to the lower end of the vertical bar 42 of the leg support member 40 via a pivot 82 so as to enable back-and-forth rotation of the vertical bar 74 with respect to the vertical bar 42. The foot joint hinge 80 has a hinge element 84 so that it can rotate in a lateral direction of the wearer around the hinge 84 in addition to back-and-forth rotation around the pivot 82.

Next, a power generator assembly 100 is explained in detail with reference to FIGS. 2 and 3. The power generator 100 comprises a hip joint electric motor 110, which is a power generator for the hip joint, and a knee joint electric motor 120, which is a power generator for the knee joint, on the same axis.

The power generator 100 comprises a cylindrical fixed case member 102 and an intermediate coupling cylinder 108 rotatably engaged inside the fixed case member 102. The fixed case member 102 is provided with an attaching piece 104 extending outward at which it is attached to a hinge 106 mounted to the lower end of the pelvis frame 12 of the pelvis support member 10 so that it can rotate in a lateral-direction of the wearer.

The hip joint electric motor 110 is a rotary motor comprising a stator member 112 and a rotor member 114 mounted inside the stator member 112 such that it can rotate with respect to the stator member 112 around their axis. The stator member 112 is secured by bolts to the external surface of an end 102A of the fixed case member 102.

The intermediate coupling cylinder 108 has, on its end 108A, a ring extension 108B which rotatably engages with an central opening 102B provided to the end 102A of the fixed case member 102. The rotor member 114 of the hip joint electric motor 110 is secured by bolts to the ring extension 108B of the intermediate coupling cylinder 108. Thus, the intermediate coupling cylinder 108 and the rotor member 114 of the hip joint electric motor 110 rotate in an integrated manner.

The intermediate coupling cylinder 108 is provided with a flange 108C at the other end (i.e., the end opposite to the end 108A). The flange 108C is secured by bolts to an output member 116. The output member 116 has, in an integrated manner, an arm 116A extending radially outward. The arm 116A is secured by bolts to the vertical bar 22 of the thigh support member 20 at an attaching portion 118. The attaching portion 118 includes a plurality of bolt holes so that the arm 116A can be secured to the vertical bar 22 in a length-adjustable manner.

The knee joint electric motor 120 is a rotary motor comprising a stator member engaged inside the intermediate coupling cylinder 108, and a rotor member 124 mounted inside the stator member 122 such that it can rotate with respect to the stator member 122 around the axis. The stator member 122 is secured by bolts to the output member 116. Therefore, the stator member 122 of the knee joint electric motor 120 is integrally connected to the rotor member 114 of the hip joint electric motor 110.

The rotor member 124 of the knee joint electric motor 120 is secured by bolts to an output member 126. The output member 126 is rotatably-fitted into a central opening 116B formed in the output member 116 of the hip joint electric motor 110 and protrudes outward from the central opening 116B.

The output member 126 has, in an integrated manner, an arm 126A extending radially outward. As shown in FIG. 1, the arm 126A is pivotally connected to the upper end of a link 94 of the power transmitting mechanism 90 by a pivot pin 92.

The shaft 62 of the knee joint hinge 60 is fixed to the upper end of the vertical bar 42 of the leg support member 40 and to an end of an arm 96 which is a component of the power transmitting mechanism 90. Thus the arm 96 is fixedly attached to the vertical bar 42 of the leg support member 40. The arm 96 is pivotally connected, at the other end, to the lower end of the link 94 by a pivot pin 98.

The distance between the rotation center of the rotor member 124 of the hip joint electric motor 110 and one of link 94's pivot points which is formed by the pivot pin 92 is equal to that between the center of the shaft 62 and the other link 94's pivot point which is formed by the pivot pin 98. Therefore, the power transmitting mechanism 90 forms a parallelogram linkage structure along with the vertical bar 22 for transmitting the rotation of the rotor member 124 of the knee joint electric motor 120 to the vertical bar 42 of the leg support member 40. This power transmitting mechanism 90 is disposed in front of the vertical bar 22.

The link 94 comprises an upper member 94A and lower member 94B. Both members are secured to each other by bolts at an attaching portion 99 which includes a plurality of bolt holes so that these members can be secured to each other in a length-adjustable manner.

Figure 2:
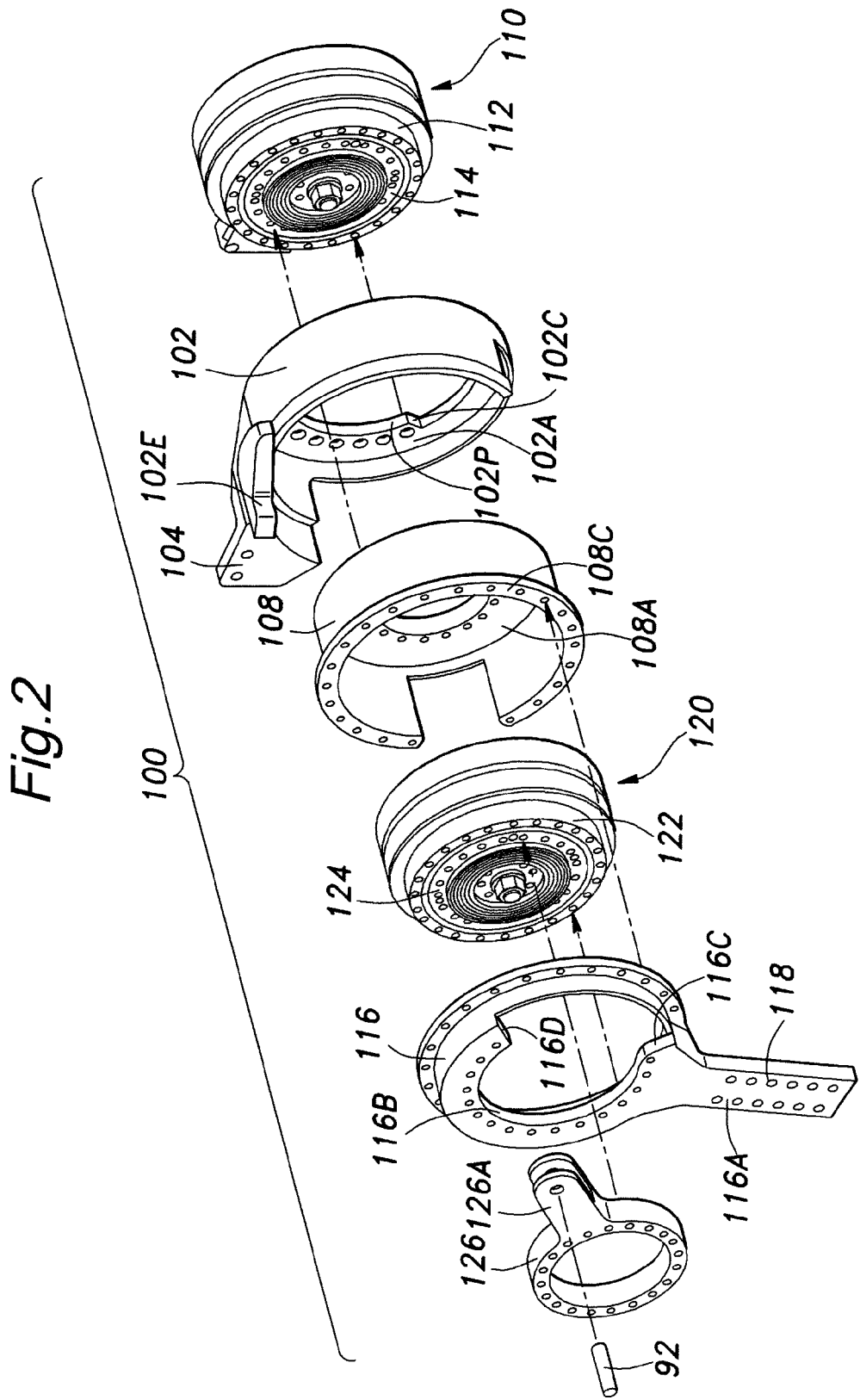
FIG. 2 is a right side exploded perspective view of the power generator used for the walking assistance device in the same embodiment.
Figure 3:
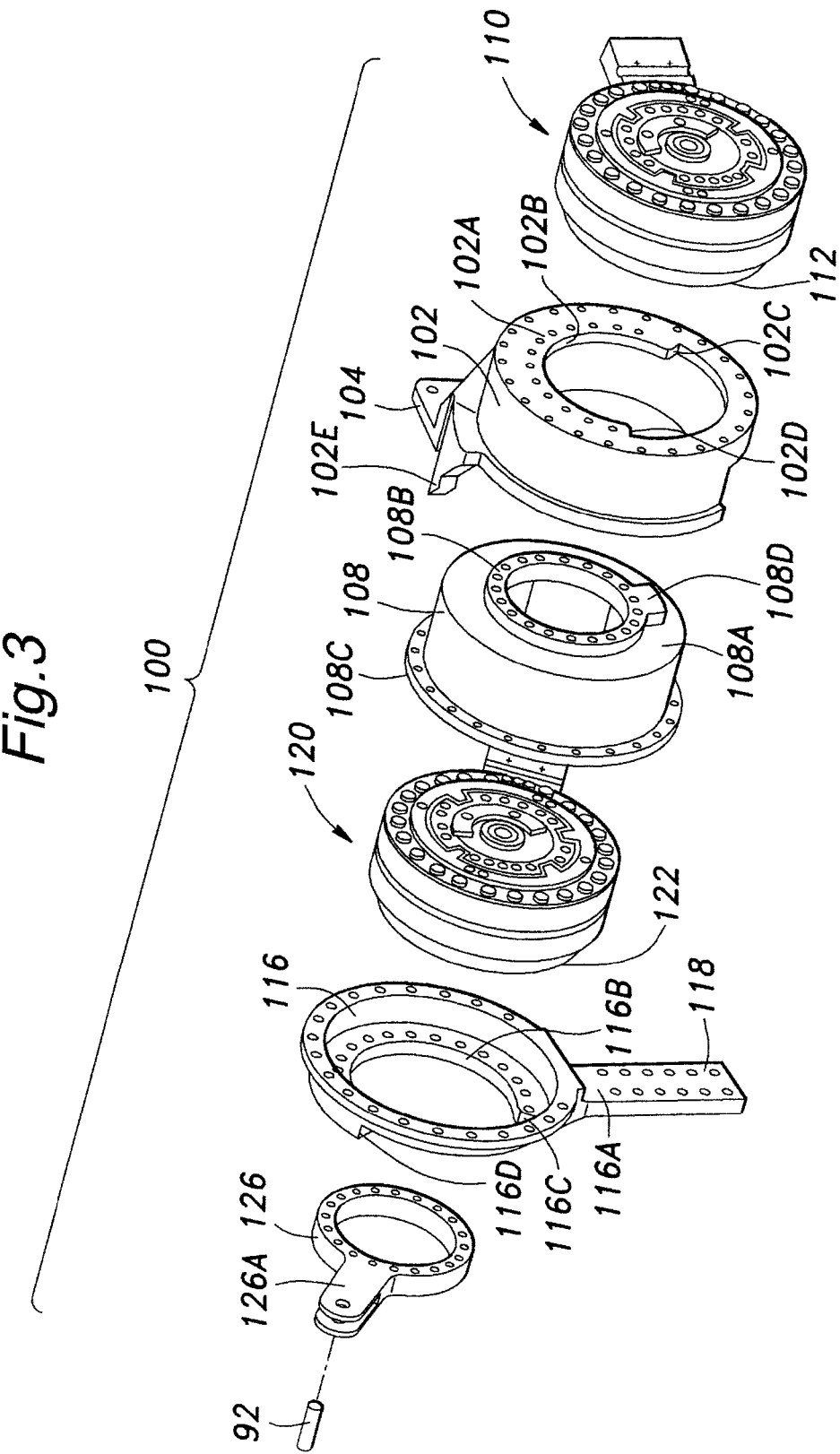
FIG. 3 is a left side exploded perspective view of the power generator used for the walking assistance device in the same embodiment.

As shown in FIGS. 2 and 3, the ring extension 108B of the intermediate coupling cylinder 108 is provided with a movable stopper 108D. The central opening 102B of the fixed case member 102 is provided with stopper walls 102C and 102D, separated from each other at a predetermined rotation angle, for holding the movable stopper 108D. Thus, the maximum rotation angle range of the rotor member 112 of the hip joint electric motor 110 with respect to the fixed case member 102 is determined by the angle between the stopper walls 102C and 102D which form the first stopper mechanism together with the movable stopper 108.

As a result, the motion of the hip joint is limited to, for example, 90 degrees of flexion, and 30 degrees of extension, thereby achieving the motion of the hip joint in normal and natural walking.

The arm 126A of the output member 126 of the knee joint electric motor 120 serves as a movable stopper. The central opening 116B of the output member 116 of the hip joint electric motor 110 is provided with stopper walls 116C and 116D, each separated from each other at a predetermined rotation angle, for abutting and holding the arm 126A. Thus, the maximum rotation angle range of the rotor member 124 of the knee joint electric motor 120 with respect to the rotor member 114 of the hip joint electric motor 110 is determined by the angle between the stopper walls 116C and 116D which form the second stopper mechanism together with the arm 126A.

As a result, the motion of the knee joint is limited to, for example, 90 degrees of flexion, and 0 degree of extension, thereby achieving the motion of the knee joint in normal and natural walking.

As a third stopper mechanism for determining the maximum rotation angle range of the rotor member 124 of the knee joint electric motor 120 with respect to the fixed case member 102, a stopper 102E is integrally-mounted to the fixed case member 102 for limiting the rotation of the arm 126A of the output member 126 in a door-stop manner.

In this embodiment, although the rotation ranges of the hip joint and the knee joint are set to be 90 degrees of flexion—30 degrees of extension and 0 degree of extension—90 degrees of flexion, respectively, which are safe in terms of each joint motion, if the wearer flexes the hip joint 90 degrees and extends the knee joint (0 degree of extension) the wearer may over-lengthen and damage his/her knee tendon. This is caused by the biarticular muscle structure of the hamstrings located in the back part of the thigh and linking the pelvis to the leg.

The third stopper mechanism is provided to prevent such a lesion of the hamstrings by preventing the extension of the knee joint from 45 degrees of flexion when the hip joint is flexed 90 degrees. Thus, by mounting a mechanical stopper for the output member 126 of the knee joint electric motor 120 to the stator portion of the hip joint electric motor 110, the extension angle of the knee joint becomes dependent to and limited by the rotation angle of the hip joint.

When using the walking assistance device of the above configuration, the wearer places his/her feet on the sole supporting plates 72 of the foot support members 70, wears the pelvis support member on the pelvis, fastens the abdominal belt 14, and puts on the thigh support member 20 with the frontal thigh pad 28 and dorsal thigh pad 30 abutting the frontal and dorsal part of thigh, respectively.

The pelvis member 10 is provided with a power supply unit and control unit (not shown). The control unit is an electronic control unit having micro computer, and inputs sensor signals provided from a six axis power sensor (not shown) mounted on the connection sites between the pad support members 24, 26 and vertical bar 22 and/or the connection sites between the pad support members 44, 46 and vertical bar 42, as well as signals provided from a floor reaction force sensor (not shown) mounted on the sole supporting plate 72, and thus controls the motion of hip joint electric motor 110 and the knee joint electric motor 120.

According to this control, the hip joint electric motor 110 is driven, and the rotation of the rotor 114 is transmitted to the thigh support member 20 via the intermediate connecting member 108 and output member 116. The knee joint electric motor 120 is also driven, and the rotation of the rotor 124 is transmitted to the leg support member 20 via the output member 126 and power-transmitting mechanism 90. Accordingly, walking-assisting force is generated and provided to the thigh and leg of the wearer, thereby achieving walking assistance.

In this walking assistance, as the frontal thigh pad 28 and the dorsal thigh pad 30 abut the frontal and dorsal part of the thigh, the walking-assisting force can be surely provided to the thigh. And since the leg frontal pad 48 and leg dorsal pad 50 abut the leg at different heights, the rotation torque enabling the appropriate motion of the leg around the knee joint for walking can be effectively provided to the leg while minimizing the discomfort that the wearer may feel.

In this performance, as the maximum rotation angle range of the rotor member 112 of the hip joint electric motor 110 with respect to the fixed case member 102 and the maximum rotation angle of the rotor member 124 of the knee joint electric motor 120 with respect to the rotor member 112 of the hip joint electric motor 110 are determined by the angle between the stopper walls 102C and 102D, and the angle between the stopper walls 116C and 116D, respectively, the motion of the hip joint and that of the knee joint in normal and natural walking are achieved, thereby ensuring an appropriate walking assistance without hampering the natural walking sense.

As described above, according to the walking assistance device of this embodiment, as the knee joint electric motor 120 is disposed at a position corresponding to a side part of the hip joint of the wearer along with the hip joint electric motor 110 instead of a position corresponding to the knee joint, the load on the hip joint electric motor becomes less as compared to when the knee joint electric motor is disposed on the knee. In addition, the increase in the inertia mass of the knee joint which would be caused if the knee joint electric motor 120 were attached to the knee joint can be avoided, thereby preventing the walking sense of the wearer from being hampered by such increase in the knee joint inertia mass. Therefore an appropriate walking assistance is achieved while reducing the discomfort that the wearer may feel. Furthermore, the walking assistance device can be configured such that the inertia mass of the device decreases in the direction from the thigh support member to the leg support member, thereby enabling walking assistance without hampering the natural walking sense.

As the knee joint electric motor 120 is attached to the rotor member 114 of the hip joint electric motor 110, when the hip joint rotates according to the rotation of the hip joint electric motor 110, it displaces the knee joint, and the knee joint electric motor 120 rotates according to the displacement of the knee joint, and thus the rotation of the knee joint electric motor 120 necessary for an appropriate rotation of the knee joint is easily determined based on the current position of the knee joint, which has been changed by the rotation of the hip joint.

Figure 4:
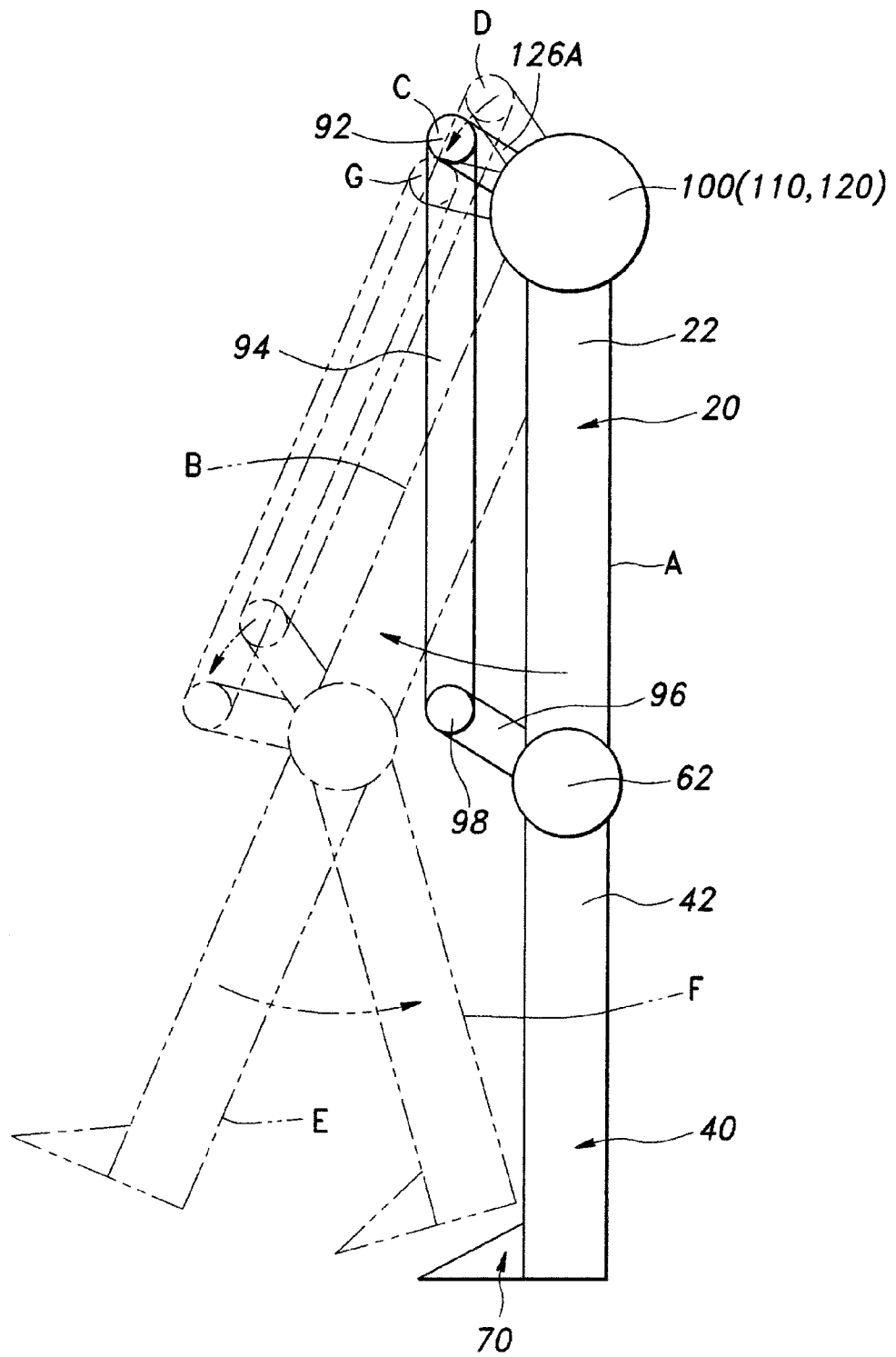
FIG. 4 is a schematic view showing the performance of the walking assistance device in the same embodiment.

For example, as shown in FIG. 4, when the thigh support member 20 rotates from A to B according to the rotation of the hip joint electric motor 110, as a result, the output member 126 of the knee joint electric motor 120 rotates from C to D at the same rotation angle as that of the thigh support member 20 (i.e. the angle between A and B). In this case, the leg support member 40 can be rotated, for example from E to F, by rotating the output member 126 of the knee joint electric motor 120 from D to G at the same rotation angle as that between E and F.

In addition, due to the hinge 106 which connects the power generator assembly to the pelvis support member 10 in a manner that enables the power generator assembly 100 to rotate with respect to the pelvis support member 10 in a lateral direction of the wearer, as well as to the hinge element 64 which enables the knee joint hinge 60 to rotate in a lateral direction of the wearer, the wearer can spread his/her legs laterally.

Furthermore, as the foot support members 70 support the feet of the wearer, the weight load of the walking assistance device can be dispersed on wearer's feet. In addition, because of the foot joint hinge 80, the feet lack motion freedom other than plantar flexion and dorsal flexion, therefore even if the wearer is almost incapable of moving and controlling his/her legs, the foot inversion and eversion can be prevented. Thus, the feet are restrained in order to maintain their motion stability during walking. Moreover, since the sole receiving plates 72 of the foot supporting members 70 receive floor reaction force, the wearer receives less floor reaction force, and thus the load on the feet of the wearer can be reduced significantly.

Another embodiment of the walking assistance device of the present invention is described hereinafter with reference to FIGS. 5 and 6.

In this embodiment, an upper arm 131 is fixed to the vertical bar 22 in proximity with its upper end such that it extends forward. The arm 96 of the knee joint hinge 60 extends forward and is connected at an end thereof to an end of the upper arm 131 with a flexible wire 132.

The arm 126A of the knee joint electric motor 120 is provided with a roller 133 at an end thereof. When the knee joint electric motor 120 rotates the arm 126A, the roller 133 selectively provides tense to the wire 132.

Except for this configuration, this embodiment is substantially the same as the aforementioned embodiment.

Figure 6:
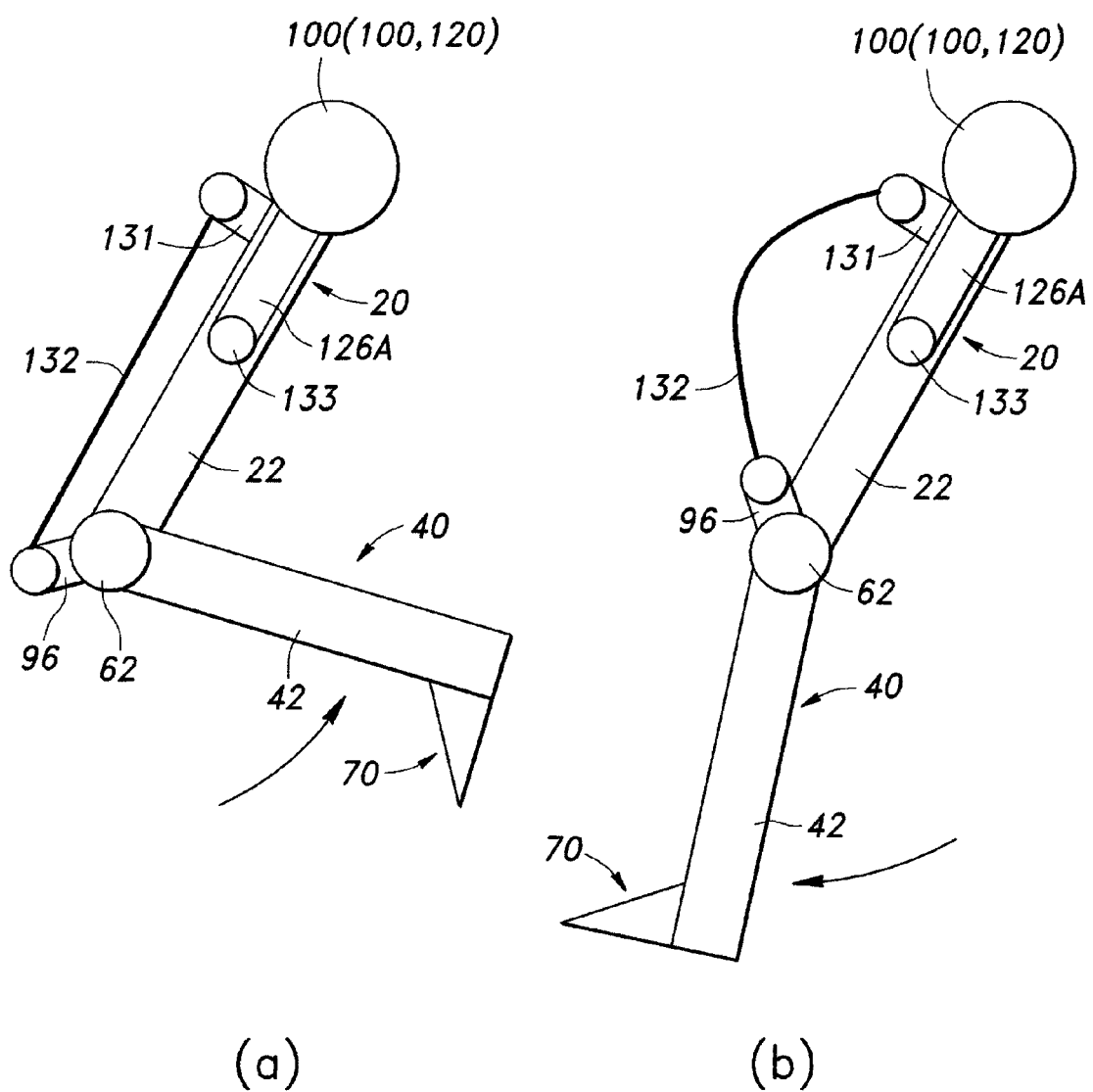
FIGS. 6(a) and (b) are schematic views showing another embodiment of the walking assistance device of the present invention in an idling position.

FIGS. 5(*a*) and (*b*) show the walking assistance device of the present invention in a standing position, while FIGS. 6(*a*) and (*b*) show the walking assistance device of the present invention in an idling position.

In the standing position, the knee joint electric motor 120 rotates the arm 126A in a clockwise direction as seen in the figure, and thus the roller 133 provides tense to the wire 132. The wire 132, as being tensed, assists the extension of the knee joint.

In the idling position, as the knee joint electric motor 120 does not rotate, the arm 126A does not rotate either, remaining in the position where it cannot provide tense to the wire 132, and thus the wire does not provide assisting force to the knee joint. Therefore, in the idling position, the wearer can freely moves the knee because of the slack of the wire 132.

In the standing and idling position mentioned above, the knee joint electric motor 120 and the wire 132 act similarly to rectus femoris, thereby achieving natural walking sense.

We claim:

1. A walking assistance device comprising:
   a pelvis support member adapted to be worn on a hip of a wearer;
   a thigh support member adapted to be worn on a thigh of the wearer;
   a leg support member adapted to be worn on a leg of the wearer;
   a knee joint hinge disposed at a position corresponding to a side part of a knee of the wearer and connecting the leg support member to the thigh support member in a manner that enables back-and forth rotation of the leg support member with respect to the thigh support member; and
   a power generator assembly mounted to the pelvis support member at a position corresponding to a side part of a hip joint of the wearer;
   wherein the power generator assembly comprises a hip joint power generator and a knee joint power generator each having an output member, with the output member of the hip joint power generator being connected to the thigh support member in a power-transmittable manner and the output member of the knee joint power generator being connected to the leg support member via a power transmitting mechanism which transmits power generated by the knee joint power generator to the leg support member wherein the power generator assembly is supported at the pelvis support member via a hinge in a manner that enables the power generator assembly to rotate with respect to the pelvis support member in a lateral direction of the wearer.

2. The walking assistance device according to claim 1, wherein the power generator assembly further comprises a fixed case member which is mounted on the pelvis support member, and the hip joint power generator and the knee joint power generator each comprise an electric motor having a stator member and a rotor member connected to the corresponding output member, the stator member of the hip joint power generator being fixedly attached to the fixed case member, and the stator member of the knee joint power generator being fixedly attached to the output member of the hip joint power generator and connected to the rotor member of the hip joint power generator.

3. The walking assistance device according to claim 2, further comprising:
   a first stopper mechanism for determining a maximum rotation angle range of the rotor member of the hip joint power generator with respect to the fixed case member; and
   a second stopper mechanism for determining a maximum rotation angle range of the rotor member of the knee joint power generator with respect to the rotor member of the hip joint power generator.

4. The walking assistance device according to claim 3, further comprising a third stopper mechanism for determining a maximum rotation angle range of the rotor member of the knee joint power generator with respect to the fixed case member.

5. The walking assistance device according to claim 1, wherein the knee joint hinge has a hinge element enabling the knee joint hinge to rotate in a lateral direction of the wearer.

6. The walking assistance device according to claim 1, wherein the thigh support member comprises a frontal thigh pad for abutting the frontal part of the thigh of the wearer, and a dorsal thigh pad for abutting the dorsal part of the thigh of the wearer.

7. The walking assistance device according to claim 1, wherein the leg support member comprises a frontal leg pad for abutting the frontal part of the leg of the wearer near the knee and a dorsal leg pad, positioned at a lower height compared to the frontal pad, for abutting the dorsal part of the leg of the wearer near a malleolus.

8. The walking assistance device according to claim 1, further comprising:
   a foot support member for supporting a foot of the wearer;
   a foot joint hinge disposed at a position corresponding to a side part of a foot joint of the wearer and connecting the foot support member to the leg support member in a manner that enables back-and-forth rotation of the foot support member with respect to the leg support member.

9. The walking assistance device according to claim 8, wherein the foot support member comprises a sole support portion for supporting a sole of the wearer and receiving floor reaction force.

10. The walking assistance device according to claim 1, wherein the power transmitting mechanism forms a parallelogram linkage structure along with a vertical bar.

11. The walking assistance device according to claim 1, wherein the power transmitting mechanism comprises a flexible wire connecting the thigh support member to the knee joint hinge and a tension-providing member for selectively providing tension to the flexible wire using power generated by the knee joint power generator.

* * * * *